United States Patent
Khosravi et al.

(10) Patent No.: US 6,620,182 B1
(45) Date of Patent: *Sep. 16, 2003

(54) VASCULAR FILTER HAVING ARTICULATION REGION AND METHODS OF USE IN THE ASCENDING AORTA

(75) Inventors: Farhad Khosravi, San Mateo, CA (US); L. N. Hopkins, Buffalo, NY (US); Amr Salahieh, Campbell, CA (US); Jackson F. Demond, Santa Cruz, CA (US); Jeff A. Krolik, Campbell, CA (US)

(73) Assignee: Incept LLC, San Mateo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/635,734

(22) Filed: Aug. 9, 2000

Related U.S. Application Data (63) Continuation-in-part of application No. 09/364,064, filed on Jul. 30, 1999.

(51) Int. Cl.[7] .............................................. A61M 29/00
(52) U.S. Cl. ....................................... 606/200; 606/194
(58) Field of Search ................................ 606/159, 198, 606/194, 200; 604/22, 96

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | 128/2 R |
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 R |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |

(List continued on next page.)

FOREIGN PATENT DOCUMENTS

| | | | |
|---|---|---|---|
| DE | 28 21 048 | 7/1980 | A61B/17/22 |
| DE | 34 17 738 | 11/1985 | A61M/1/34 |
| DE | 40 30 998 A1 | 10/1990 | A61F/2/01 |

(List continued on next page.)

OTHER PUBLICATIONS

"Atherosclerotic Disease of the Aortic Arch as a Risk Factor of Recurrent Ischemic Stroke," *The New England Journal of Medicine*, pp. 1216–1221 (May 1996).

(List continued on next page.)

*Primary Examiner*—Gary Jackson
(74) *Attorney, Agent, or Firm*—Crompton, Seager & Tufte LLC (57) ABSTRACT

Apparatus and methods are provided for use in filtering emboli from a vessel such as the ascending aorta, wherein a vascular device comprises a support hoop having an articulation region connected near a distal end of an elongated member, a blood permeable sac affixed to the support hoop so that the support hoop forms a mouth of the blood permeable sac, a guide wire, and a delivery sheath. The articulation region comprises a reduced thickness region of the support hoop that prevents kinks from forming in the support hoop when the apparatus is contracted to its delivery state, and curved regions that close the mouth of the sac to prevent material escaping from the sac when the apparatus is collapsed for removal.

35 Claims, 7 Drawing Sheets

U.S. PATENT DOCUMENTS

| | | | |
|---|---|---|---|
| 4,650,466 A | 3/1987 | Luther | 604/95 |
| 4,662,885 A | 5/1987 | DiPisa, Jr. | 623/12 |
| 4,705,517 A | 11/1987 | DiPisa, Jr. | 623/12 |
| 4,706,671 A | 11/1987 | Weinrib | 128/348 |
| 4,723,549 A | 2/1988 | Wholey et al. | 128/344 |
| 4,728,319 A | 3/1988 | Masch | 604/22 |
| 4,733,665 A | 3/1988 | Palmaz | 128/343 |
| 4,784,928 A | 11/1988 | Kan et al. | 128/344 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660.03 |
| 4,800,882 A | 1/1989 | Gianturco | 128/343 |
| 4,807,626 A | 2/1989 | McGirr | 128/328 |
| 4,842,579 A | 6/1989 | Shiber | 606/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,898,575 A | 2/1990 | Fischell et al. | 604/22 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Gifford et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/22 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,108,419 A | 4/1992 | Reger et al. | 606/200 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,192,286 A | 3/1993 | Phan et al. | |
| 5,195,955 A | 3/1993 | Don Michael | 604/22 |
| 5,224,953 A | 7/1993 | Morgentaler | 606/192 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,329,942 A | 7/1994 | Gunther et al. | 128/898 |
| 5,330,484 A | 7/1994 | Gunther | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,366,464 A | 11/1994 | Belknap | 606/159 |
| 5,366,473 A | 11/1994 | Winston et al. | 606/198 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazerus | 623/1 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 4,842,579 A | 10/1995 | Shiber | 604/22 |
| 5,456,667 A | 10/1995 | Ham et al. | 604/107 |
| 5,462,529 A | 10/1995 | Simpson et al. | 604/101 |
| 5,476,104 A | 12/1995 | Sheahon | 128/757 |
| 5,484,418 A | 1/1996 | Quiachon et al. | 604/167 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vowerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,695,519 A | 12/1997 | Summers et al. | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,746,758 A | 5/1998 | Nordgren et al. | 606/159 |
| 5,749,848 A | 5/1998 | Jang et al. | 604/53 |
| 5,769,816 A | 6/1998 | Barbut et al. | 604/96 |
| 5,779,716 A | 7/1998 | Cano et al. | 606/114 |
| 5,792,157 A | 8/1998 | Mische et al. | |
| 5,792,300 A | 8/1998 | Inderbitzen et al. | 156/244.13 |
| 5,795,322 A | 8/1998 | Boudewijn | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,810,874 A | 9/1998 | Lefebvre | 606/200 |
| 5,814,064 A | 9/1998 | Daniel et al. | 606/200 |
| 5,817,102 A | 10/1998 | Johnson et al. | 606/108 |
| 5,827,324 A | 10/1998 | Cassell et al. | 606/200 |
| 5,833,644 A | 11/1998 | Zadno-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |
| 5,893,867 A | 4/1999 | Bagaoisan et al. | 606/198 |
| 5,895,399 A | 4/1999 | Barbut et al. | 606/159 |
| 5,902,263 A | 5/1999 | Patterson et al. | 604/22 |
| 5,906,618 A | 5/1999 | Larson, III | 606/108 |
| 5,908,435 A | 6/1999 | Samuels | 606/200 |
| 5,910,154 A | 6/1999 | Tsugita et al. | 606/200 |
| 5,911,734 A | 6/1999 | Tsugita et al. | 606/200 |
| 5,916,193 A | 6/1999 | Stevens et al. | 604/53 |

| Patent | Date | Inventor | Class |
|---|---|---|---|
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |
| 5,925,063 A | 7/1999 | Khosravi | 606/200 |
| 5,928,203 A | 7/1999 | Davey et al. | 604/247 |
| 5,928,218 A | 7/1999 | Gelbfish | 604/540 |
| 5,934,284 A | 8/1999 | Plaia et al. | 128/898 |
| 5,935,139 A | 8/1999 | Bates | 606/159 |
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/198 |
| 5,954,745 A | 9/1999 | Gertler et al. | 606/200 |
| 5,976,172 A | 11/1999 | Homsma et al. | 606/200 |
| 5,980,555 A | 11/1999 | Barbut et al. | |
| 5,989,210 A | 11/1999 | Morris et al. | 604/22 |
| 5,989,271 A | 11/1999 | Bonnette et al. | 606/159 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,001,118 A | 12/1999 | Daniel et al. | 606/200 |
| 6,007,557 A | 12/1999 | Ambrisco et al. | 606/200 |
| 6,010,522 A | 1/2000 | Barbut et al. | 606/200 |
| 6,013,085 A | 1/2000 | Howard | 606/108 |
| 6,027,520 A | 2/2000 | Tsugita et al. | 606/200 |
| 6,042,598 A | 3/2000 | Tsugita et al. | |
| 6,051,014 A | 4/2000 | Jang | 606/200 |
| 6,051,015 A | 4/2000 | Maahs | |
| 6,053,932 A | 4/2000 | Daniel et al. | 606/200 |
| 6,059,814 A | 5/2000 | Ladd | 606/200 |
| 6,066,149 A | 5/2000 | Samson et al. | |
| 6,068,645 A | 5/2000 | Tu | 606/200 |
| 6,086,605 A | 7/2000 | Barbut et al. | 606/200 |
| 6,117,154 A | 9/2000 | Barbut et al. | |
| 6,129,739 A | 10/2000 | Khosravi | 606/200 |
| 6,136,016 A | 10/2000 | Barbut et al. | |
| 6,142,987 A | 11/2000 | Tsugita | 604/500 |
| 6,152,946 A | 11/2000 | Broome et al. | 606/200 |
| 6,165,200 A | 12/2000 | Tsugita et al. | 606/200 |
| 6,168,579 B1 | 1/2001 | Tsugita | 604/96.01 |
| 6,171,327 B1 | 1/2001 | Daniel et al. | 606/200 |
| 6,171,328 B1 | 1/2001 | Addis | |
| 6,179,851 B1 | 1/2001 | Barbut et al. | 606/159 |
| 6,179,859 B1 | 1/2001 | Bates et al. | 606/200 |
| 6,179,861 B1 | 1/2001 | Khosravi et al. | 606/200 |
| 6,203,561 B1 | 3/2001 | Ramee et al. | 606/200 |
| 6,206,868 B1 | 3/2001 | Parodi | |
| 6,214,026 B1 | 4/2001 | Lepak et al. | 606/200 |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |

FOREIGN PATENT DOCUMENTS

| | | | |
|---|---|---|---|
| DE | 199 16 162 | 10/2000 | |
| EP | 0 200 688 | 11/1986 | A61B/17/22 |
| EP | 0 293 605 A1 | 12/1988 | A61F/2/02 |
| EP | 0 411 118 A1 | 2/1991 | A61M/25/00 |
| EP | 0 427 429 A1 | 5/1991 | A61M/25/10 |
| EP | 0 437 121 B1 | 7/1991 | A61F/2/02 |
| EP | 0 472 334 A1 | 2/1992 | A61F/2/02 |
| EP | 0 472 368 A2 | 2/1992 | A61B/17/22 |
| EP | 0 533 511 A1 | 3/1993 | A61M/29/02 |
| EP | 0 655 228 A1 | 11/1994 | A61F/2/02 |
| EP | 0 686 379 A2 | 6/1995 | A61F/2/06 |
| EP | 0 696 447 A2 | 2/1996 | A61F/2/06 |
| EP | 0 737 450 A1 | 10/1996 | A61F/2/01 |
| EP | 0 743 046 A1 | 11/1996 | A61F/2/01 |
| EP | 0 759 287 A1 | 2/1997 | A61F/2/01 |
| EP | 0 771 549 A2 | 5/1997 | A61F/2/01 |
| EP | 0 784 988 A1 | 7/1997 | A61M/5/165 |
| EP | 0 852 132 A1 | 7/1998 | A61F/2/01 |
| EP | 1 127 556 A2 | 8/2001 | |
| FR | 2 580 504 | 10/1986 | A61M/1/00 |
| FR | 2 643 250 A1 | 8/1990 | A61B/17/00 |
| FR | 2 666 980 | 3/1992 | A61F/2/02 |
| FR | 2 694 687 | 8/1992 | |
| FR | 2 768 326 A1 | 3/1999 | A61F/2/01 |
| GB | 2 020 557 B | 11/1979 | A61B/17/50 |
| JP | 8-187294 A | 7/1996 | A61M/29/00 |
| SU | 764684 | 9/1980 | A61M/25/00 |
| WO | WO 92/03097 | 3/1992 | A61B/17/00 |
| WO | WO 94/14389 | 7/1994 | A61F/2/02 |
| WO | WO 94/24946 | 11/1994 | A61B/17/22 |
| WO | WO 96/01591 | 1/1996 | A61B/17/22 |
| WO | WO 96/10375 | 4/1996 | A61F/2/06 |
| WO | WO 96/19941 | 7/1996 | A61B/17/00 |
| WO | WO 96/23441 | 8/1996 | A61B/5/00 |
| WO | WO 96/33677 | 10/1996 | A61F/11/00 |
| WO | WO 97/17100 | 5/1997 | A61M/29/00 |
| WO | WO 97/27808 | 8/1997 | A61B/17/22 |
| WO | WO 97/42879 | 11/1997 | A61B/17/00 |
| WO | WO 98/02084 | 1/1998 | |
| WO | WO 98/02112 | 1/1998 | A61F/2/01 |
| WO | WO 98/23322 | 6/1998 | A61M/29/00 |
| WO | WO 98/33443 | 8/1998 | A61B/17/22 |
| WO | WO 98/34673 | 8/1998 | A61B/31/00 |
| WO | WO 98/36786 | 8/1998 | A61M/5/32 |
| WO | WO 98/38920 | 9/1998 | A61B/17/22 |
| WO | WO 98/38929 | 9/1998 | A61B/17/00 |
| WO | WO 98/39046 | 9/1998 | A61M/25/00 |
| WO | WO 98/39053 | 9/1998 | A61M/29/00 |
| WO | WO 98/46297 | 10/1998 | A61M/29/00 |
| WO | WO 98/47447 | 10/1998 | A61F/2/06 |
| WO | WO 98/49952 | 11/1998 | A61B/17/32 |
| WO | WO 98/50103 | 11/1998 | A61M/29/00 |
| WO | WO 98/51237 | 11/1998 | A61F/2/01 |
| WO | WO 98/55175 | 12/1998 | A61M/29/00 |
| WO | WO 99/09895 | 3/1999 | A61B/17/12 |
| WO | WO 99/22673 | 5/1999 | A61F/2/01 |
| WO | WO 99/23976 | 5/1999 | A61F/2/01 |
| WO | WO 99/25252 | 5/1999 | A61B/17/00 |
| WO | WO 99/30766 | 6/1999 | A61M/29/00 |
| WO | 0 934 729 | 8/1999 | A61B/17/22 |
| WO | WO 99/40964 | 8/1999 | A61M/29/02 |
| WO | WO 99/42059 | 8/1999 | A61F/2/06 |
| WO | WO 99/44510 | 9/1999 | A61B/17/00 |
| WO | WO 99/44542 | 9/1999 | A61F/2/06 |
| WO | WO 99/55236 | 11/1999 | A61B/17/00 |
| WO | WO 99/58068 | 11/1999 | A61B/17/22 |
| WO | WO 00/07521 | 2/2000 | |
| WO | WO 00/07655 | 2/2000 | A61M/29/00 |
| WO | WO 00/09054 | 2/2000 | A61F/7/12 |
| WO | WO 00/16705 | 3/2000 | A61B/17/22 |

| | | | |
|---|---|---|---|
| WO | WO 00/49970 | 8/2000 | ............ A61F/2/01 |
| WO | WO 00/53120 | 9/2000 | |
| WO | WO 00/67664 | 11/2000 | |
| WO | WO 00/67665 | 11/2000 | |
| WO | WO 00/67666 | 11/2000 | |
| WO | WO 00/67668 | 11/2000 | |
| WO | WO 00/67669 | 11/2000 | |
| WO | WO 01/05462 | 1/2001 | |
| WO | WO 01/08595 | 2/2001 | |
| WO | WO 01/08596 | 2/2001 | |
| WO | WO 01/08742 | 2/2001 | |
| WO | WO 01/08743 | 2/2001 | |
| WO | WO 01/10320 | 2/2001 | |
| WO | WO 01/15629 | 3/2001 | |
| WO | WO 01/21077 | 3/2001 | |
| WO | WO 01/21100 | 3/2001 | |
| WO | WO 01/26726 | 4/2001 | |
| WO | WO 01/35857 | 5/2001 | |
| WO | WO 01/43662 | 6/2001 | |
| WO | WO 01/47579 | 7/2001 | |
| WO | WO 01/49208 | 7/2001 | |
| WO | WO 01/49209 | 7/2001 | |
| WO | WO 01/49215 | 7/2001 | |
| WO | WO 01/49355 | 7/2001 | |
| WO | WO 01/52768 | 7/2001 | |
| WO | WO 01/58382 | 8/2001 | |
| WO | WO 01/60442 | 8/2001 | |
| WO | WO 01/67989 | 9/2001 | |
| WO | WO 01/70326 | 9/2001 | |
| WO | WO 01/72205 | 10/2001 | |
| WO | WO 01/87183 | 11/2001 | |
| WO | WO 01/89413 | 11/2001 | |
| WO | WO 01/91824 | 12/2001 | |

OTHER PUBLICATIONS

"Endovascular Grafts, Stents Drive Interventional Radiology Growth," *Cardiovascular Device Update*, 2(3):1–12 (Mar. 1996).

"Protuding Atheromas in the Thoracic Aortic and Systemic Embolization," pp. 423–427 American College of Physicians (1991).*

"Recognition and Embolic Potential of Intraaortic Atherosclerotic Debris," American College of Cardiology (Jan. 1991).*

Cragg, Andrew et al., "A New Percutaneous Vena Cava Filger," *AJR*, 141:601–604.*

Cragg, Andrew et al., "Nonsurgical Placement of Arterial Endoprosthesis: A New Technique Using Nitinol Wire," *AJR*, pp. 261–263 (Apr. 1983).*

Diethrich et al., "Percutaneous Techniques for Endoluminal Carotid Interventions," *J. Endovasc. Surg.*, 3:182–202 (1996).*

Haissaguerre et al., "Spontaneous Initiation of Atrial Fibrillation by Ectopic Beats Originating in the Pulmonary Veins," *The New England Journal of Medicine*, 339(10):659–666 (Sep. 1988).*

Jordan, Jr. et al., "Microemboli Detected by Transcranial Doppler Monitoring . . . ," *Cardiovascular Surgery*, 7(1)33–38 (Jan. 1999).*

Lesh, "Can Catheter Ablation Cure Atrial Fibrillation?" *ACC Current Journal Review*, pp. 38–40 (Sep./Oct. 1997).*

Lund et al., "Long–Term Patentcy of *Ductus Arteriosus* After Balloon Dilation: an Experimental Study," *Laboratory Investigation*, 69(4):772–774 (Apr. 1984).*

Marache et al., "Percutaneous Transluminal Venous Angioplasty . . . ," *American Heart Journal*, 125(2 Pt 1):362–366 (Feb. 1993).*

Mazur et al., "Directional Atherectomy with the Omnicath™: A Unique New Catheter System," *Catheterization and Cardiovascular Diagnosis*, 31:17–84 (1994).*

Moussa, MD, Issaam "Stents Don't Require Systemic Anticoagulation . . . But the Technique (and Results) Must be Optimal," *Journal of Invasive Cardiol.*, 8(E):3E–7E, (1996).*

Nakanishi et al., "Catheter Intervention to Venous System Using Expandable Metallic Stents," *Rinsho Kyobu Geka*, 14(2):English Abstract Only (Apr. 1994).*

Onal et al., "Primary Stenting for Complex Atherosclerotic Plaques in Aortic and Iliac Stenoses," *Cardiovascular & Interventional Radiology*, 21(5):386–392 (1998).*

Theron et al., "New Triple Coaxial Catheter System for Carotid Angioplasty with Cerebral Protection," *American Journal of Neuroradiology*, 11:869–874 (1990).*

Tunick et al., "Protruding atherosclerotic plaque in the aortic archo f patients with systemic embolization: A new finding seen by transesophageal echocardiography," *American Heart Journal* 120(3):658–660 (Sep. 1990).*

Waksman et al., "Distal Embolization is Common After Directional Atherectomy . . . ," *American Heart Journal*, 129(3):430–435 (1995).

Wholey, Mark H. et al., "PTA and Stents in the Treatment of Extracranial Circulation," *The Journal of Invasive Cardiology: vol. 8/Supplement E*, Health Management Publications, Inc., 1996, pp. 25E–30E.

Fadali, A. Moneim, "A filtering device for the prevention of particulate embolization during the course of cardiac surgery", *Surgery*, vol. 64(3), pp. 634–639 (Sep. 1968).

* cited by examiner

VASCULAR FILTER HAVING ARTICULATION REGION AND METHODS OF USE IN THE ASCENDING AORTA

REFERENCE TO RELATED APPLICATIONS

This application is a continuation-in-part of U.S. patent application Ser. No. 09/364,064 filed Jul. 30, 1999. This application is also related to the subject matter of co-pending U.S. patent applications Ser. Nos. 09/470,706 filed Dec. 23, 1999, U.S. Pat. No. 6,224,621 and 09/470,857 filed Dec. 23, 1999, U.S. Pat. No. 6,129,739 both of which are incorporated herein by reference.

FIELD OF THE INVENTION

The present invention relates to apparatus and methods for filtering or removing matter from within the vascular system. More particularly, the present invention provides a low profile self-expanding vascular device useful in the ascending aorta for capturing emboli generated during vascular procedures.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of cannulas, cross clamps or occlusion balloons during bypass surgery, or stents and stent-grafts to treat vascular disease also involves the introduction of foreign objects into the bloodstream and may result in the formation of clots or release of emboli. Such particulate matter, if released into the bloodstream, also may cause infarction or stroke.

Numerous previously known methods and apparatus have been proposed to reduce the risk of embolism. U.S. Pat. No. 5,833,644 to Zadno-Azizi et al., for example, describes the use of balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as angioplasty balloons or stent delivery systems, are advanced along the guide wire. The filter is designed to capture emboli generated during treatment of the stenosis while permitting blood to flow through the filter. Similar filter systems are described in U.S. Pat. No. 4,723,549 to Wholey et al., and U.S. Pat. No. 5,827,324 to Cassell et al.

One disadvantage of radially expandable filter systems such as described in the foregoing patents is the relative complexity of the devices, which typically comprise numerous parts. Connecting more than a minimal number of such parts to a guide wire generally reduces the ability of the guide wire to negotiate tortuous anatomy and increases the profile of the device in its delivery configuration. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly and is expected to result in a large delivery profile.

In view of the foregoing disadvantages of previously known apparatus and methods, it would be desirable to provide a vascular device, e.g., for use as a vascular filter in the ascending aorta, that, overcomes such disadvantages, and employs few components.

It also would be desirable to provide a vascular device that is capable of being contracted to a small delivery profile.

It further would be desirable to provide a vascular device that is capable of being advanced into position from the downstream direction of blood flow.

It still further would be desirable to provide a vascular device that reduces the risk of emboli or thrombus removed from the vessel wall escaping from the device when the device is collapsed and removed.

SUMMARY OF THE INVENTION

In view of the foregoing, it is an object of the present invention to provide a vascular device, e.g., for use as a vascular filter in the ascending aorta, that overcomes disadvantages associated with previous vascular filters and thrombectomy/embolectomy devices, and employs few components.

It is another object of the present invention to provide a vascular device that is capable of being contracted to a small delivery profile.

It is yet another object of the present invention to provide a vascular device that is capable of being advanced into position from the downstream direction of blood flow.

It is a further object of this invention to provide a vascular device that reduces the risk of emboli or thrombus removed from the vessel wall escaping from the device when the device is collapsed and removed.

These and other objects of the present invention are accomplished by providing a vascular device suitable for use as a vascular filter in the ascending aorta that comprises a blood permeable sac affixed at its perimeter to a support hoop having an articulation region. The support hoop is attached in a distal region of an elongated member, such as a guide wire, and supports a distally-oriented mouth of the sac when the device is deployed in a vessel. In accordance with the principles of the present invention, the support hoop includes a reduced-thickness articulation region that enables the support hoop to be contracted to very small radii of curvature without the problems of increased stiffness and kinking of previously known devices. The vascular device may therefore be used with delivery sheaths having diameters as small as 0.060".

The support hoop preferably also has a curved profile that prevents the articulation region, when folded, from damaging the wall of the vessel. The curved profile also permits the device to effectively contact the walls of the vessel and reduce emboli or thrombus removed from the vessel wall from bypassing the sac. The articulation region, when combined with a support hoop having a curved profile, causes the sides of the support hoop to fold inwards towards one-another when the vascular device is collapsed into a sheath for removal. This, in turn, closes the mouth of the sac and reduces the potential for emboli or thrombus to be released from the vascular device during removal.

Methods of using the vascular device of the present invention are also provided, particularly in the context of a vascular filter placed in the ascending aorta.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
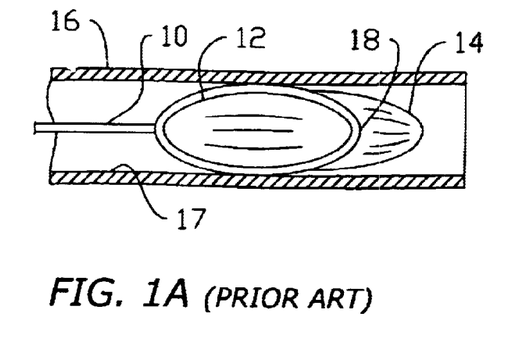
FIGS. 1A and 1B are, respectively, a side sectional side of a previously known vascular device contracted within a delivery sheath and an end view of that vascular device deployed in a vessel.
Figure 1B:
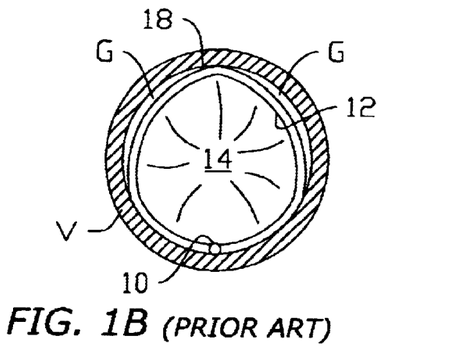

Referring to FIGS. 1A and 1B, some of the disadvantages associated with previously known vascular devices, such as the emboli filters described in the above-mentioned International Publication WO 98/39053, are described. Vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of a vessel.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.117" or smaller are used, a hoop of nitinol or multi-strand nitinol cable having a diameter of 0.012" may form kink 18. Kink 18 in turn may apply relatively high localized pressure and friction against wall 17 of sheath 16, thereby making the vascular filter difficult to deploy. In particular, the kink may impale wall 17 of delivery sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability of the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular device of the present invention solves the above-described disadvantages, providing a vascular device, suitable for use as a vascular filter in, for example, the ascending aorta, with a self-expanding support hoop that is sufficiently thick to radially expand and urge a blood permeable sac into engagement with the vessel wall, but which includes an articulation region that overcomes the problems associated with kinking. In particular, the vascular device of the present invention includes a reduced thickness articulation region and a pre-formed curved profile that avoids the difficulties of previously known systems while providing a high degree of efficacy in capturing emboli or thrombus, and ease of deployment and retrieval.

Figure 2A:
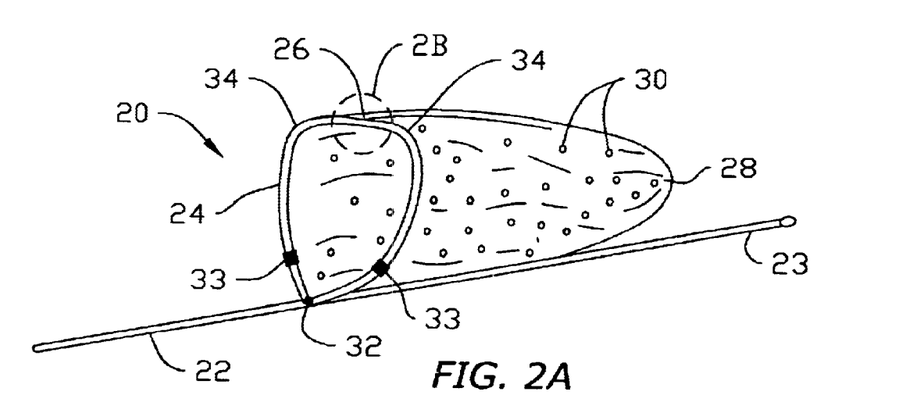
FIGS. 2A and 2B are, respectively, a perspective view of a vascular device constructed in accordance with the principles of the present invention in a deployed state, and a detailed view of the articulation region of the device of FIG. 2A.
Figure 2B:
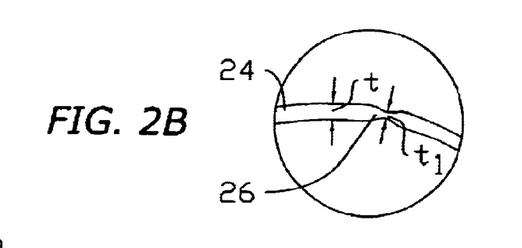

Referring now to FIGS. 2A and 2B, vascular device 20 constructed in accordance with the principles of the present invention, illustratively an embolic filter, comprises guide wire 22, support hoop 24 having articulation region 26, and blood permeable sac 28 affixed to support hoop 24. Sac 28 is coupled to support hoop 24 so that the support hoop forms an opening for the sac. Support hoop 24 preferably is connected to guide wire 22 near end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof, and includes openings or pores 30 that permit blood cells to pass through the sac substantially unhindered, while capturing any larger emboli that may be released during a procedure such as angioplasty or stent placement. In a preferred embodiment, sac 28 has openings or pores 30 in a range of about 20 to 400 microns in diameter, and more preferably, about approximately 80 microns. These pore sizes will permit red blood cells (which have a diameter of approximately 5 microns) to easily pass through the sac.

Pores 30 are preferably formed by a laser drilling process. For example, a thin sheet of the flexible biocompatible material may be thermoformed to create sac 28, for example, by stretching the sheet over a mandrel, by dip forming, or by blow molding. Sac 28 may alternatively be fabricated from an extruded tube of the biocompatible material. A flat metal mask, with tiny holes approximately the size of pores 30, may then be placed in front of the sac. A laser having a beam diameter equal to or greater than the diameter of the material illuminates the mask. The laser beam passes through the holes in the mask and strikes the material, thereby forming pores 30 in sac 28.

Laser drilling may also be accomplished with a laser having a beam diameter approximately the size of pores 30, in which case pores 30 may drilled individually. Sac 28 may alternatively comprise a woven material, for example, formed from the above-mentioned polymers, having a pore diameter determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular device 20, described hereinafter, support hoop 24 folds in half and collapses to fit within a small diameter delivery sheath. When vascular device 20 is in a deployed state, as depicted in FIG. 2A, support hoop 24 resumes its pre-formed shape. Support hoop 24 preferably comprises nitinol wire, although it may also be formed from a multistrand nitinol cable, spring tempered stainless steel, or other super-elastic material.

In accordance with the principles of the present invention, support hoop 24 includes one or more reduced-thickness articulation regions 26 and curved regions 34. As depicted in FIG. 2B, articulation region 26 includes a region having reduced thickness $t_1$ compared to thickness t of the remainder of support hoop 24. Articulation region 26 and curved regions 34 enable support hoop 24 to fold with a predetermined shape when vascular device 20 is collapsed to a contracted state for delivery or retrieval.

In FIG. 2B, articulation region 26 is depicted as a localized reduction in the thickness of support hoop 24, as may be achieved using, for example, conventional grinding, chemical etching, or electroless polishing processes. Alternatively, support hoop 24 may be continuously tapered along its circumference, so that articulation region 26 results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In an alternative embodiment, the articulation region may comprise a gap in the support hoop. The gap may then be bridged by a portion of the blood permeable sac. This is expected to allow fabrication of the support hoop from elastic materials and may provide improved delivery and retrieval characteristics.

In a preferred embodiment of the vascular device 20 of the present invention, vascular device 20 easily fits within a delivery sheath having an inner diameter of 0.114", and more preferably, may be used with a delivery sheath having an inner diameter as small as 0.060". The deployed diameter of support hoop 24 preferably is approximately 25 mm, while guide wire 22 preferably has a diameter of 0.035". The distal end of guide wire 22 also may be tipped with a spring section, or coil tip (not shown).

Support hoop 24 preferably is constructed of 0.012" nitinol wire tapered, for example, by a grinding, chemical etching, or electroless polishing process, to 0.005" at articulation region 26. Specifically, articulation region 26 preferably consists of a length about 0.15" long and having a diameter of 0.005", coupled on either side to curved regions 34. Each of curved regions 34 includes a length of wire that is tapered from a diameter of 0.012" to a diameter of 0.005" over a length of about 0.070". Support hoop 24 also may include radiopaque features, such as gold or platinum bands 33, spaced at intervals around the circumference of support hoop 24, or a coil of radiopaque material wrapped around the support hoop, or a gold plated coating.

Figure 3:
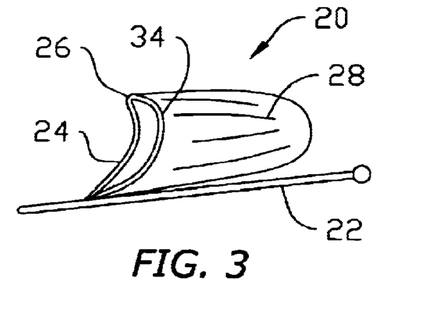
FIG. 3 is a perspective view of the vascular device of the present invention in a folded configuration, prior to removal.
Figure 4:
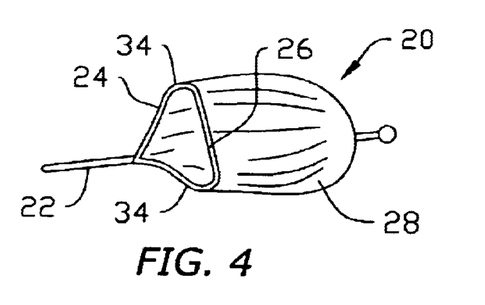
FIG. 4 is a plan view of the vascular device of FIG. 2A.

With respect to FIGS. 3 and 4, additional features of vascular device 20 are described. FIG. 3 depicts vascular device 20 of FIG. 2A in a contracted state, while FIG. 4 illustrates a directional change in support hoop 24 preferably caused by the presence of curved regions 34. In the embodiment depicted in FIG. 4, curved regions 34 illustratively are configured to orient articulation region 26 in a direction parallel to the axis of guide wire 22.

Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac than would otherwise be possible, without increasing the risk of material escaping from the device when the sac is collapsed for retrieval.

Use of a smaller or shallower sac also enables vascular device 20 to be delivered in a smaller delivery sheath, having an inner diameter as small as 0.060" for the preferred embodiment. To prevent bunching during retrieval or further decrease the size of sac 28, the sac may be affixed to guide wire 22 along a length of the blood permeable sac. Sac 28 may also taper along its length.

Figures 5A, 5B:
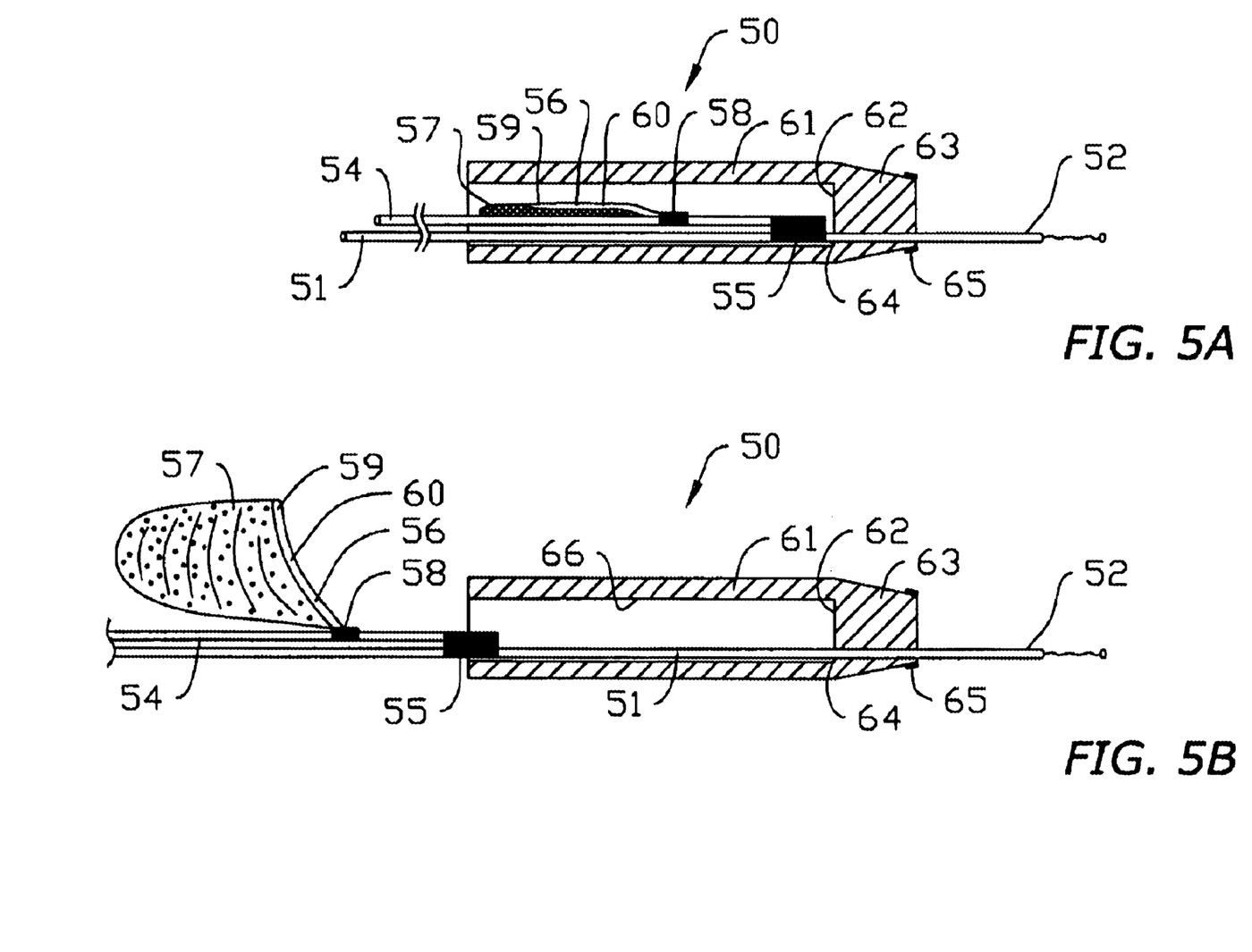
FIGS. 5A and 5B are side sectional views of an embodiment of the vascular device of the present invention suited for use as a vascular filter in the ascending aorta, shown, respectively, in the contracted state and in the deployed state.

Referring now to FIGS. 5A and 5B, an embodiment of the vascular device of the present invention suited for use as a vascular filter in the ascending aorta is described. Vascular device 50 comprises guide wire 51 having distal end 52. Elongated member 54 is rigidly attached to linear bearing 55, which is slidably attached to guide wire 51. Elongated member 54 therefore may be advanced over guide wire 51 to contact internal face 62 of delivery sheath 61, and advance the delivery sheath. Delivery sheath 61 comprises tapered end 63 having lumen 64, in which distal end 52 of guide wire 51 is rigidly received, and preferably also comprises radiopaque band 65. Distally-facing support hoop 56 has blood permeable sac 57 attached to its perimeter. Support hoop 56 is, in turn, connected to elongated member 54 at attachment point 58. Articulation region 59 and curved regions 60 of support hoop 56 enable the sides of the support hoop to fold together and become elongated when urged within cavity 66 of delivery sheath 61 by distal motion of elongated member 54 with guide wire 51 held stationary, or vice versa.

Figure 6A:
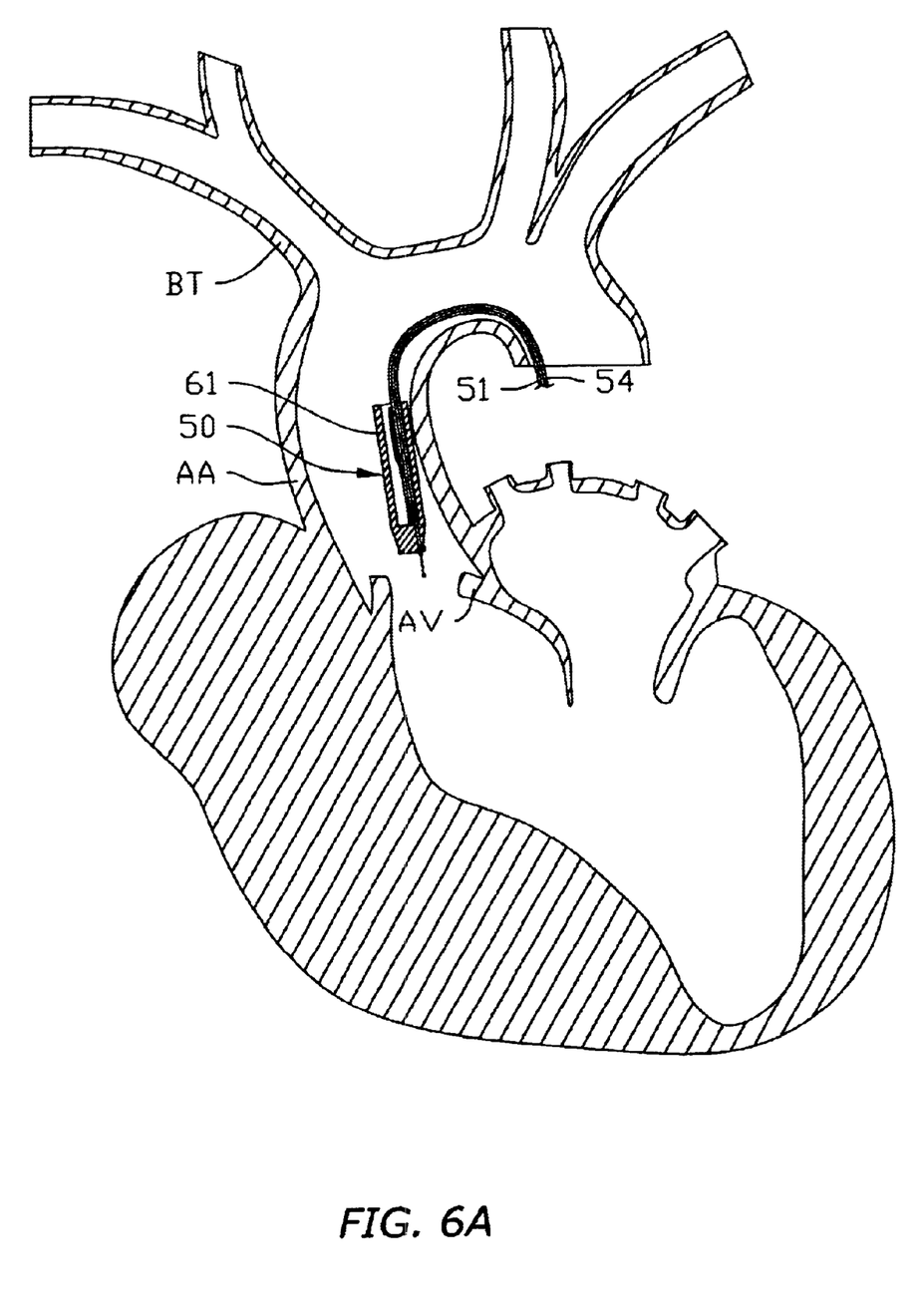
FIGS. 6A–6C are side sectional views depicting a method of deploying, using and retrieving the vascular device of FIGS. 5 in the ascending aorta.
Figure 6B:
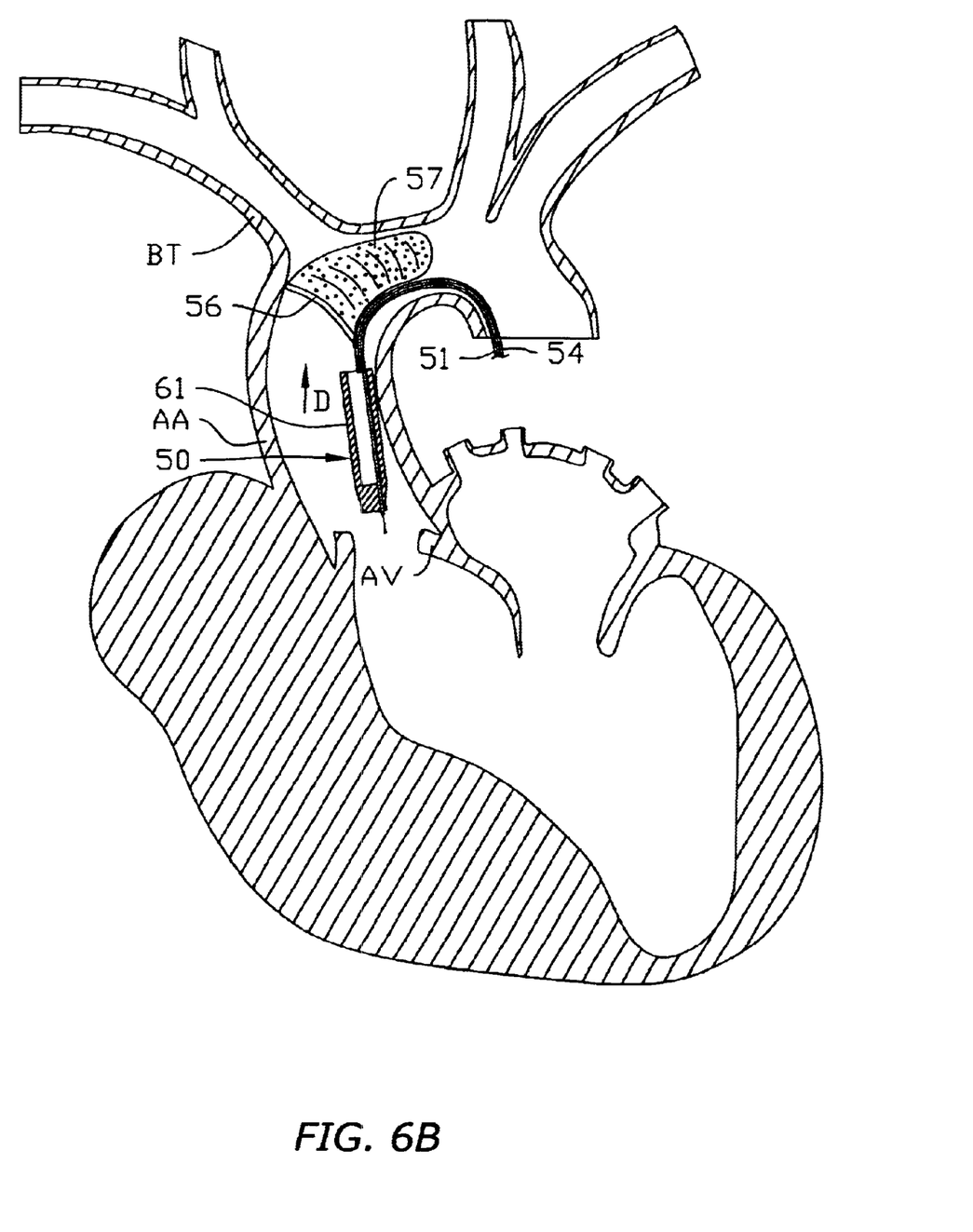
Figure 6C:
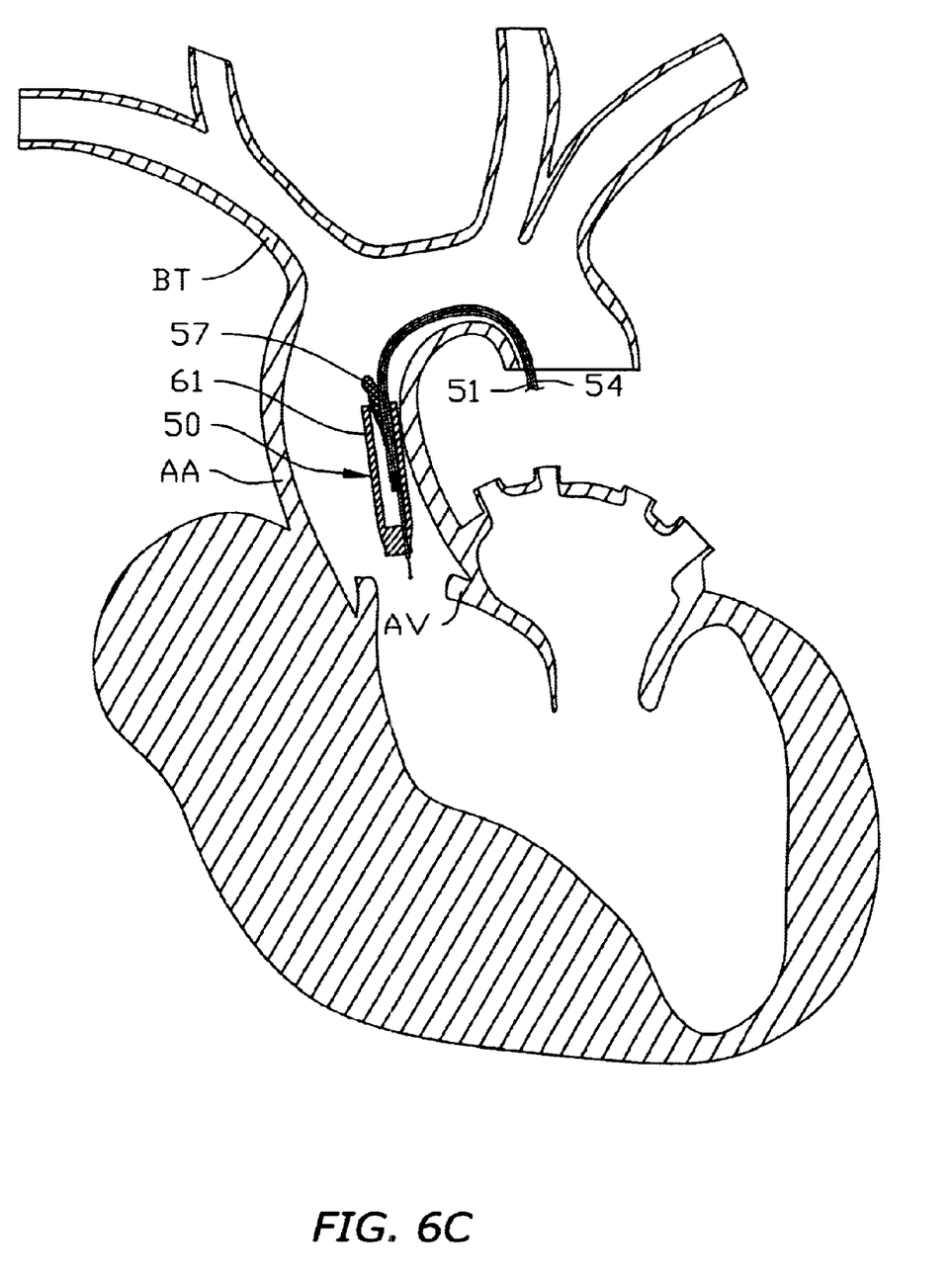

With reference to FIGS. 6A–6C, a method of deploying, using and retrieving vascular device 50 of FIGS. 5 in the ascending aorta is described. In FIG. 6A, vascular device 50 is disposed in its contracted state within delivery sheath 61. Guide wire 51, with delivery sheath 61 attached, is manipulated into position within ascending aorta AA such that vascular device 50 is located proximal of aortic valve AV but distal of brachiocephalic trunk BT. The device is positioned using well-known percutaneous techniques, for example, based on the position of radiopaque band 65 under a fluoroscope.

Referring now to FIG. 6B, with vascular device 50 in position, elongated member 54 is retracted proximally while guide wire 51 and attached sheath 61 are held stationary. Alternatively, elongated member 54 may be held stationary while guide wire 51 and delivery sheath 61 are advanced (in this case, distal end 52 of guide wire 51 is not initially advanced as far and lies just proximal of aortic valve AV only after deployment of vascular device 50). In either case, when vascular device 50 is no longer confined within delivery sheath 61, support hoop 56 expands to seal against the walls of the ascending aorta AA. Blood continues to flow unimpeded through ascending aorta AA in direction D. Emboli generated upstream (distal) of vascular device 50 by, for example, cannulas, occlusion balloons, cross-clamps, and interventional instruments, such as angioplasty catheters, atherectomy devices, or stent delivery systems, are captured within sac 57.

With respect to FIG. 6C, once the interventional procedure is complete and generated emboli have been captured within sac 57, elongated member 54 is advanced distally while guide wire 51 and delivery sheath 61 are held stationary. The sides of support hoop 56 collapse together to close the mouth of sac 57 (see FIG. 3). Additional distal advancement of member 54 urges support hoop 56 and sac 57 at least partially within cavity 66 of sheath 61. As depicted in FIG. 6C, only a portion of support hoop 56 near articulation region 59 and a distal portion of sac 57 extend out of delivery sheath 61. Alternatively, the entirety of hoop 56 and sac 57 may be retracted within sheath 61. Guide wire 51 is then retracted proximally, and sheath 61 contacts bearing 55 at internal face 62, thereby causing the whole of vascular device 50 with any trapped emboli to be withdrawn proximally.

Figure 7A:
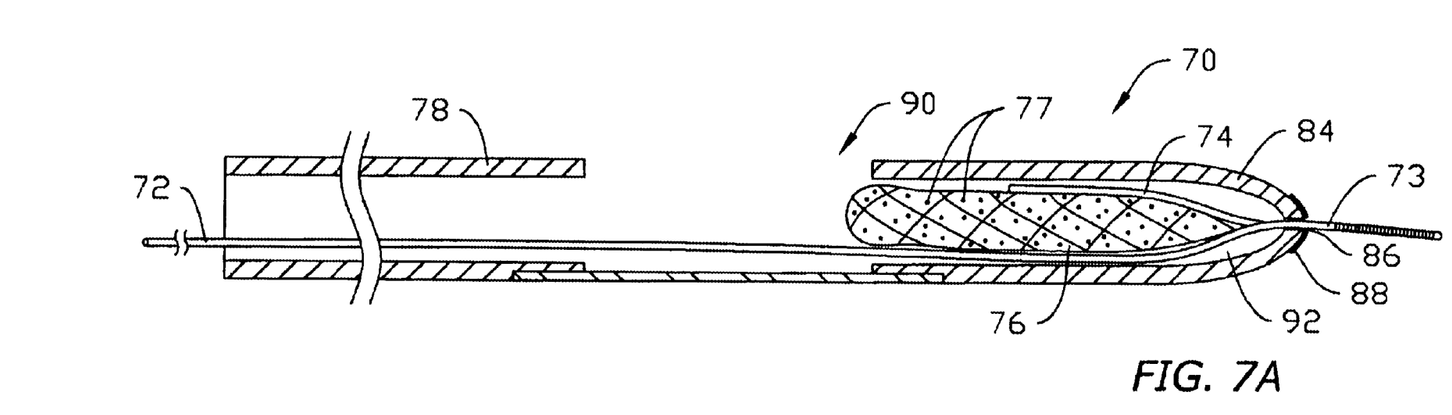
FIGS. 7A and 7B are side sectional views of another embodiment of the present invention suited for use as an aortic filter, shown, respectively, in the contracted state and in the deployed state.
Figure 7B:
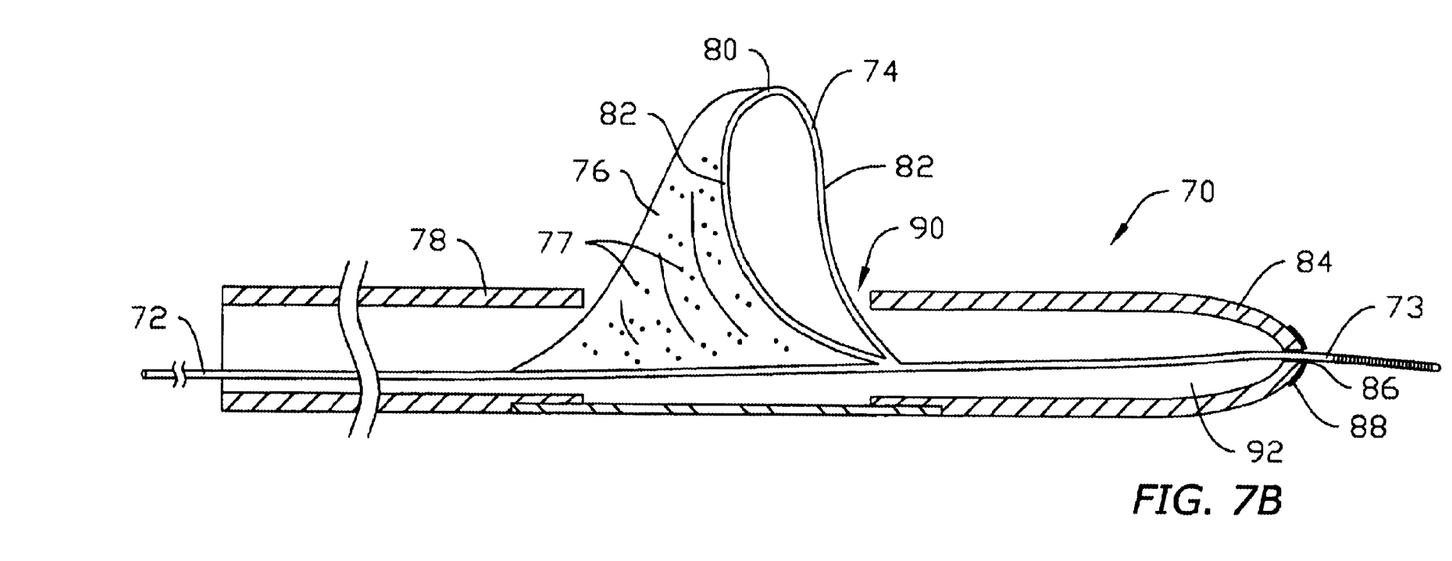

Referring now to FIGS. 7A and 7B, another embodiment of the present invention suited for use as a vascular filter in the ascending aorta is described. Vascular device 70 comprises guide wire 72, distally facing support hoop 74, blood permeable sac 76, and delivery sheath 78. Guide wire 72 has distal end 73, near which distally-facing support hoop 74 is attached, and is preferably 0.035" in diameter. Support hoop 74 comprises articulation region 80 disposed between curved regions 82. Blood permeable sac 76 is attached at its perimeter to support hoop 74 and along its length to guide wire 72. Sac 76 tapers along its length and comprises pores 77.

Vascular device 70 is disposed within delivery sheath 78. Sheath 78 comprises tapered end 84 having lumen 86, in which distal end 73 of guide wire 72 is slidably received, and preferably also comprises radiopaque band 88. Sheath 78 further comprises window 90, located just proximal of support hoop 74 and sac 76 when vascular device 70 is located within cavity 92 of sheath 78, in the contracted delivery configuration of FIG. 7A.

Articulation region 80 and curved regions 82 of support hoop 74 enable contraction to the delivery configuration by causing the sides of the support hoop to fold together and become elongated when urged within cavity 92. Hoop 74 is urged within cavity 92 by distally advancing guide wire 72 while sheath 78 is held stationary (or by proximally retracting sheath 78 while guide wire 72 is held stationary). Vascular device 70 is then expanded to the deployed configuration by proximally retracting guide wire 72 relative to sheath 78 so that support hoop 74 is able to expand through window 90.

Vascular device 70 may be used in a manner similar to that described hereinabove with respect to FIGS. 6. The device is advanced in the delivery configuration to a position in a patient's ascending aorta that allows support hoop 74 to expand to the deployed configuration through window 90 and seal against the walls of the vessel at a location just distal of the brachiocephalic trunk. Emboli generated upstream are captured within sac 76, while blood continues to flow unimpeded through the vessel. Upon completion of the filtering procedure, support hoop 74 and sac 76 are contracted back to the delivery configuration within cavity 92 of sheath 78, and vascular device 70 is removed from the patient's vasculature.

Figure 8A:
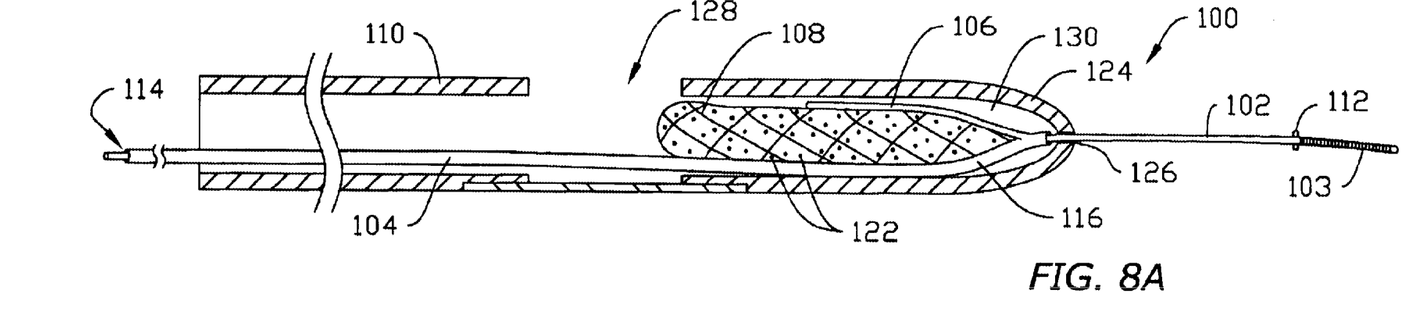
FIGS. 8A and 8B are side sectional views of an alternative embodiment of the apparatus of FIGS. 7, shown, respectively, in the contracted state and in the deployed state.
Figure 8B:
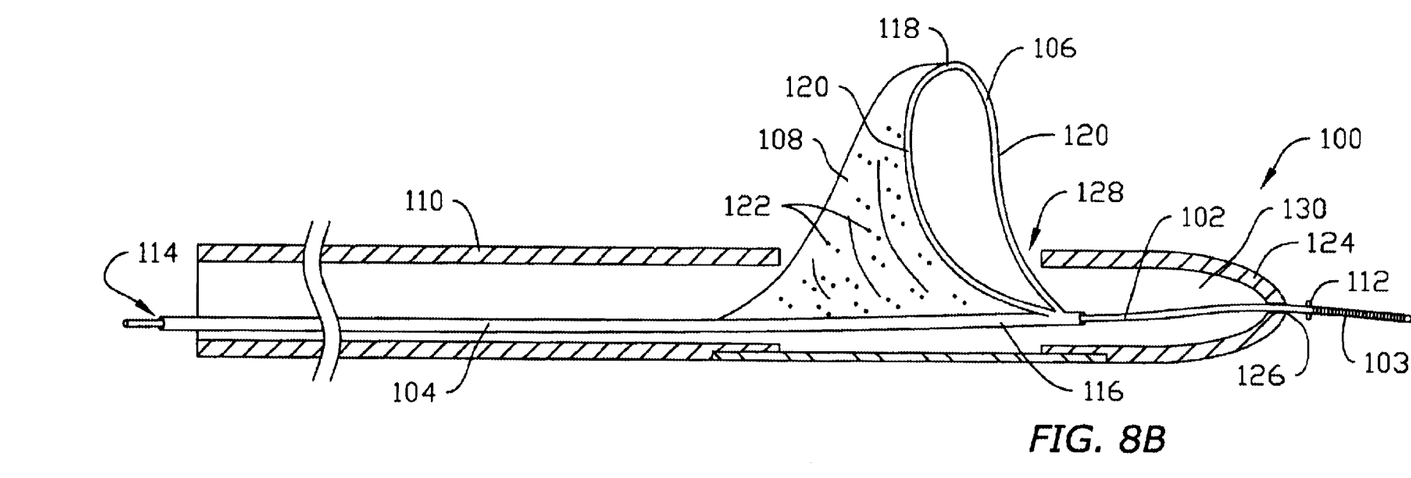

With reference to FIGS. 8A and 8B, an alternative embodiment of the apparatus of FIGS. 7 is described. Vascular device 100 comprises guide wire 102, deployment sheath 104, distally facing support hoop 106, blood permeable sac 108, and delivery sheath 110. Guide wire 102 has distal end 103 comprising position indication restraint 112, which may be radiopaque. Guide wire 102 is preferably about 0.035" in diameter. Deployment sheath 104 comprises lumen 114 configured to slidably receive guide wire 102, and further comprises distal end 116 to which distally-facing support hoop 106 is attached. The deployment sheath preferably has a wall thickness in the range of 0.001" to 0.002", and a preferred external diameter in the range of 0.037" to 0.040", thereby facilitating reception of guide wire 102 within lumen 114. Preferred fabrication materials for deployment sheath 104 include biocompatible materials, such as polyamide and polyethylene tetraphlalate.

As discussed previously, support hoop 106 is attached to deployment sheath 104. Hoop 106 comprises articulation region 118 disposed between curved regions 120. Blood permeable sac 108 is attached at its perimeter to support hoop 106 and along its length to deployment sheath 104. Sac 108 tapers along its length and comprises pores 122.

Vascular device 100 is disposed within delivery sheath 110. Sheath 110 comprises tapered end 124 having lumen 126, which is sized to slidably receive distal end 103 of guide wire 102 while not allowing deployment sheath 104 to pass therethrough. Delivery sheath 110 further comprises window 128 and cavity 130. Window 128 is located just proximal of support hoop 106 and sac 108 when vascular device 100 is in the contracted delivery configuration within cavity 130, as seen in FIG. 8A. The delivery sheath may also comprise a radiopaque band (not shown) to facilitate proper positioning.

Articulation region 118 and curved regions 120 of support hoop 106 enable contraction to the delivery configuration of FIG. 8A by causing the sides of the support hoop to fold together and become elongated when urged within cavity 130. Hoop 106 is urged within cavity 130 by distally advancing deployment sheath 104 while delivery sheath 110 is held stationary. Delivery sheath 110 may be held stationary directly or, alternatively, may be held stationary by contacting the delivery sheath against restraint 112 of guide wire 102, and then holding guide wire 102 stationary. Hoop 106 may also be urged within cavity 130 by proximally retracting delivery sheath 110 while deployment sheath 104 is held stationary. Vascular device 100 may then be expanded from the delivery configuration to the deployed configuration of FIG. 8B by proximally retracting deployment sheath 104 relative to delivery sheath 110 so that support hoop 106 is able to expand through window 128.

A method of using vascular device 100 is now provided. Guide wire 102 is advanced through a patient's vasculature until distal end 103 is positioned within the patient's ascending aorta just proximal of the aortic valve, as determined, for example, by position indication restraint 112 under a fluoroscope. With vascular device 100 in the delivery configuration within cavity 130 of delivery sheath 110, a proximal end of guide wire 102 is passed through lumen 126 of the delivery sheath and lumen 114 of deployment sheath 104. Delivery sheath 110 is then advanced along guide wire 102 until it abuts against restraint 112. Vascular device 100 may alternatively be advanced along with guide wire 102 in a single step, in a manner similar to that described with respect to vascular device 70 of FIGS. 7.

With vascular device 100 advanced and positioned, hoop 106 is expanded through window 128 to the deployed configuration and seals against the walls of the vessel at a location just distal of the brachiocephalic trunk. Emboli generated upstream are captured within sac 108, while blood continues to flow unimpeded through the vessel. Upon completion of the filtering procedure, support hoop 106 and sac 108 are contracted back to the delivery configuration within cavity 130 of delivery sheath 110, and vascular device 100 is removed from the patient's vasculature.

As will of course be understood by those of skill in the art of catheter design, FIGS. 5–8 have not been drawn to scale in order to clarify certain structural aspects of the preferred embodiments. For example, in FIGS. 5 and 6, the diameter of delivery sheath 61 is approximately an order of magnitude smaller than either the inner diameter of the ascending aorta or the full deployed height of support hoop 56.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus suitable for filtering emboli comprising:
   an elongated member having a distal region;
   a support hoop attached to the distal region, the support hoop having an articulation region; and
   a blood permeable sac affixed to the support hoop, the support hoop forming a distally-facing mouth of the blood permeable sac.

2. The apparatus of claim 1 further comprising a delivery sheath having a proximally-facing cavity for accepting the elongated member, support hoop and blood permeable sac.

3. The apparatus of claim 2 further comprising a guide wire slidably attached to the elongated member.

4. The apparatus of claim 3 wherein the elongated member abuts against an interior surface of the cavity so that distal translation of the elongated member is transmitted to the delivery sheath.

5. The apparatus of claim 2, wherein the delivery sheath further comprises a radiopaque feature.

6. The apparatus of claim 3 further comprising a lumen extending through the cavity, the guide wire rigidly received within the lumen.

7. The apparatus of claim 2 further comprising a lumen extending through a distal end of the delivery sheath to permit the elongated member to pass therethrough.

8. The apparatus of claim 2 further comprising a window disposed proximal of the cavity.

9. The apparatus of claim 8, wherein the apparatus has a deployed state, wherein the support hoop expands through the window to engage an interior wall of a patient's vessel, and a delivery state, wherein the apparatus has a contracted configuration to permit insertion of the elongated member, support hoop, and blood permeable sac within the cavity of the delivery sheath.

10. The apparatus of claim 3, wherein the elongated member comprises a deployment sheath.

11. The apparatus of claim 10 further comprising a lumen extending through a distal end of the delivery sheath to permit the guide wire to pass therethrough.

12. The apparatus of claim 11 further comprising a position indication restraint attached to a distal end of the guide wire.

13. The apparatus of claim 12, wherein the restraint is radiopaque.

14. The apparatus of claim 10 further comprising a window disposed proximal of the cavity.

15. The apparatus of claim 14, wherein the apparatus has a deployed state, wherein the support hoop expands through the window to engage an interior wall of a patient's vessel, and a delivery state, wherein the apparatus has a contracted configuration to permit insertion of the deployment sheath, support hoop, and blood permeable sac within the cavity of the delivery sheath.

16. The apparatus of claim 1, wherein the blood permeable sac comprises a biocompatible material.

17. The apparatus of claim 16, wherein the biocompatible material comprises a material chosen from a group consisting of polyethylene, polypropylene, polyurethane, polyester, polyethylene tetraphlalate, nylon and polytetrafluoroethylene.

18. The apparatus of claim 16, wherein the biocompatible material is formed into the blood permeable sac by a thermoforming process.

19. The apparatus of claim 1, wherein the blood permeable sac comprises a plurality of pores.

20. The apparatus of claim 19, wherein each one of the plurality of pores has a diameter in a range of 20 to 400 microns.

21. The apparatus of claim 1, wherein the blood permeable sac comprises a plurality of pores formed by laser drilling.

22. The apparatus of claim 1, wherein the support hoop comprises a super-elastic material.

23. The apparatus of claim 22, wherein the super-elastic material comprises a nickel-titanium alloy.

24. The apparatus of claim 22, wherein the super-elastic material comprises a spring tempered stainless steel.

25. The apparatus of claim 1, wherein the support hoop comprises a wire having a thickness that tapers to a minimum thickness at the articulation region.

26. The apparatus of claim 1, wherein the apparatus has a deployed state, wherein the support hoop engages an interior wall of a patient's vessel, and a delivery state, wherein the apparatus has a contracted configuration to permit insertion of the elongated member, support hoop, and blood permeable sac within the delivery sheath.

27. The apparatus of claim 26, wherein the support hoop is folded at the articulation region when the apparatus is in the delivery state.

28. The apparatus of claim 26, wherein the mouth of the blood permeable sac is closed when the apparatus is in the contracted configuration, thereby preventing emboli from escaping from the blood permeable sac.

29. The apparatus of claim 28 wherein opposite sides of the support hoop close towards one another when the apparatus is contracted to its contracted configuration.

30. The apparatus of claim 1, wherein the support hoop further comprises a radiopaque feature.

31. The apparatus of claim 1, wherein the blood permeable sac is affixed to the elongated member along a length of the blood permeable sac.

32. The apparatus of claim 1, wherein the blood permeable sac has a length and a diameter that tapers along the length.

33. The apparatus of claim 1, wherein the articulation region comprises a gap, the gap bridged by a portion of the blood permeable sac.

34. The apparatus of claim 1, wherein the support hoop comprises a wire having a thickness that is at a minimum thickness at the articulation region.

35. The apparatus of claim 34, wherein the support hoop comprises a wire having a first end and a second end, wherein the first end is proximate the second end at the articulation region.

* * * * *